(12) United States Patent
Tsujimoto et al.

(10) Patent No.: US 7,229,773 B1
(45) Date of Patent: Jun. 12, 2007

(54) SCREENING METHOD FOR APOPTOSIS-SUPPRESSING OR-PROMOTING SUBSTANCE

(75) Inventors: Yoshihide Tsujimoto, Toyonaka (JP); Shigeomi Shimizu, Osaka (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/958,215

(22) PCT Filed: Apr. 5, 2000

(86) PCT No.: PCT/JP00/02200

§ 371 (c)(1),
(2), (4) Date: Oct. 5, 2001

(30) Foreign Application Priority Data

Apr. 8, 1999 (JP) .......................................... H11-101888

(51) Int. Cl.
*G01N 33/53* (2006.01)

(52) U.S. Cl. .......................... 435/7.1; 424/9.1; 424/9.2; 424/9.321; 424/9.34; 530/350; 536/23.1

(58) Field of Classification Search .................. 435/7.1, 435/4; 424/9.1, 9.2, 9.321, 9.34; 530/350; 536/23.1
See application file for complete search history.

(56) References Cited

U.S. PATENT DOCUMENTS 5,702,897 A * 12/1997 Reed et al. ...................... 435/6
5,834,309 A * 11/1998 Thompson et al. .......... 435/325
6,207,133 B1 * 3/2001 Reszka et al. ............ 424/9.321

OTHER PUBLICATIONS

Huang et al, Feb. 1998, EMBO J, 17(4): 1029–1039.*
Kimmel et al.(J. Neurosurg, 66:161–171, 1987).*
Oltvai et al, 1994, Cell, 79: 189–192.*
MPSRCH search report, 2003, us–09–958–215–2–copy–7–30.rai, p. 1.*
MPSRCH search report, 2003, us–09–958–215–2.rai, pp. 1–2.*
Cleary, ML et al, 1986, Cell 47(1): 19–28, and MPSRCH search report, 2003, us–09–958–215–1.rge, pp. 2–3.*
Wunder, UR, 1991, J Membrane Biol, 123: 83–91.*
Narita et al., "Bax interacts with the permeability transition pore to induce permeability transition and cytochrome c release in isolated mitochondria" *Proc. Natl Acad. Sci. USA*, Dec. 1998, vol. 95, pp. 14681–14686.
Zamzami et al., "Mitochondrial Control of Nuclear Apoptosis", *J. Exp. Med.*, Apr. 1996, vol. 183, pp. 1533–1544.
Vander et al., "Bcl-$x_L$ Regulates the Membrane Potential and Volume Homeostasis of Mitochondria", *Cell*, Nov. 28, 1997, vol. 91, pp. 627–637.

Shimizu et al., "Bcl–2 Pprevents apoptotic mitochondrial dysfunctionby regulating proton flux", *Proc. Natl Acad. Sci. USA*, Feb. 1998, vol. 95, pp. 1455–1459.
Jürgensmeier et al., "Bax directly induces release of cytochrome c from isolated mitochondria", *Natl Acad. Sci .USA*, Apr. 1998, vol. 95, pp. 4997–5002.
Eskes et al., "Bax–induced Cytochrome C release from Mitochondria is Independent of the Permeability Transition Pore but Highly Dependent on $Mg^{2+}$ Ions", *The Journal of Cell Biology*, Oct. 5, 1998, vol. 143, No. 1, pp. 317–224.
Marzo et al., "Bax and Adenine Nucleotide Translocator Cooperate in the Mitochondrial Control of Apoptosis", *Science*, Sep. 25, 1998, vol. 281, 2027–2031.
Bernardi et al. "Recent Progress on Regulation of the Mitochondrial Permeability Transition Pore; a Cyclosporin–Sensitive Pore in the Inner Mitochondrial Membrane", *Journal of Bioenergetice and Biomembranes*, 1994, vol. 26, No. 5, pp. 509–517.
Zoratti et al., "The mitochondrial permeability transition", *Biochemica et Biophysica Acta*, 1995, 1241, pp. 139–176.
Colombini, "Voltage Gating in the Mitochondrial Channel, VDAC", *J. Membrane Biol.*, vol. 111, pp.–103–111.
Xu et al., "Bax Inhibitor–1, a Mammalian Apoptosis Suppressoe Identified by Funtional Screening in Yeast", *Molecular Cell*, Feb. 1998, vol. 1, pp. 337–346.
De Pinto et al., "A simple and rapid method for the purification of the mitochondrial porin from mammalian tissues", *Biochemica et Biophysica Acta*, 1987, 905, pp. 499–502.
Rück et al., "Reconstituted adenine nucleotide translocase forms a channel for small molecules comparable to the mitochondrial permeability transition pore", *FEBS letters*, 1998, vol. 426, pp. 97–101.
Bàthori et al., "Transport properties and inhibitor sensitivity of isolated and reconstituted porin differ from those of intact mitochondria", *Biochemica et Biophysica Acta*, 1993, 1145, pp. 168–176.
"Preparation of Cells and Reagents for Flow Cytometry" *Current Protocols in Immunology*, 1990, 5.3.1–5.3.11.

(Continued)

*Primary Examiner*—Susan Ungar
*Assistant Examiner*—Minh-Tam Davis
(74) *Attorney, Agent, or Firm*—Venable LLP; Robert Kinberg; Ann S. Hobbs

(57) ABSTRACT

To provide a screening method for an apoptosis-suppressing substance or an apoptosis-promoting substance, the application of which substances to pharmaceuticals or diagnostic drugs are expected, also to provide an apoptosis-suppressing substance or an apoptosis-promoting substance, since Bcl-2 family having apoptosis-suppressing or -promoting activities is deeply involved in many diseases.

To attain the above object, VDAC-liposomes, an indicator substance such as fluorescent-labeled cytochrome c or isotope-labeled sucrose etc. capable of passing through VDAC (voltage-dependent anion channel), and a subject substance are incubated, and then concentration changes in the indicator substance, inside and outside the VDAC-liposomes before and after the incubation, are detected in order to estimate presence or absence of the apoptosis-suppressing activity or -promoting activity of the subject substance.

7 Claims, 5 Drawing Sheets

U.S. PATENT DOCUMENTS

Daum et al., "Import of Proteins into Mitchondria", *Journal of Biological Chemistry*, 1982, vol. 257, No. 21, pp. 13028–13033.

Shimizu et al., "Retardation of chemical hypoxia–induced neurotic cell death by Bcl–2 and ICE inhibitors: possible involvement of common mediators in apoptotic and necrotic signal transductions", *Oncogene*, 1996, 12, pp. 2045–2050.

Antonsson et al., "Inhibition of Bax Channel–Forming Activity by Bcl–2", *Science*, Jul. 1997, pp. 370–372.

Minn et al., "Bcl–$x_L$ forms an ion channel in synthetic lipid membranes", *Nature*, 1997, vol. 385, pp. 353–357.

Schendel et al., "Channel formation by antiapoptotic protein Bcl–2", *Proc. Natl Acad. Sci. USA*, May 1997, vol. 94, pp. 5113–5118.

Schlesinger et al., "Comparison of the ion channel characteristics of proapoptotic BAX and antiapoptotic BCL–2", *Proc. Natl Acad. Sci. USA*, Oct. 1997, vol. 94, pp. 11357–11362.

Cheng et al., "Bax–independent inhibiton of apoptosis by Bcl–$x_L$", *NATURE*, Feb. 8, 1996, vol. 379, pp. 554–556.

Greenhalf et al., "Role mitochondria and C–terminal membrane anchor of Bcl–2 in Bax induced growth arrest and mortality in *Saccharomyces cerevisiae*", *FEBS letter*, 1996, 380, pp. 169–175.

Matsuyama et al., "The Mitochondrial $F_oF_1$—ATPase Proton Pump Is Required for Function of the Proapoptotic Protein Bax in Yeast and Mammalian Cells", *Molecular Cell*, Feb. 1998, vol. 1, pp. 327–336.

Blachly–Dyson et al., "Selectivity Changes in Site–Directed Mutants of the VDAC Ion Channel: Structural Implications", *Science*, 1990, vol. 247, 1233–1236.

Cleary et al., "Cloning and Structural Analysis of cDNAs for bcl–2 and a Hybrid bcl–2/Immunoglobulin Transcript Resulting form the t(14;18) Translocation", *Cell*, Oct. 10, 1986, vol. 47, pp. 19–28.

Boise et al., "bcl–x, a bcl–2–Related Gene That Functions as a Dominant Regulator of Apoptotic Cell Death", *Cell*, 1993, vol. 74, pp. 597–608.

Oltval et al., "Bcl–2 Heterodimerizes In Vivo with a Conserved Homolog, Bax, That Accelerates Programmed Cell Death", 1993, vol. 74, pp. 609–619.

Blachly–Dyson et al., "Cloning and Functional Expression in Yeast of Two Human Isoforms of the Outer Mitchondrial Membrane Channel, the Voltage–dependent Anion Channel", Jan. 1993, vol. 268, No. 3, pp. 1835–1841.

Shimizu et al., "BH4 domain of antiapoptotic Bcl–2 family members closes voltage–dependent anion channel and inhibits apoptotic mitochondrial changes and cell death", *Proc. Natl Acad. Sci. USA*, Mar. 28, 2000, vol. 97 No. 7, pp. 3100–3105.

Shimizu et al., "Bcl–2 family proteins regulate the release of apoptogenic cytochrome c by the mitochondrial channel VDAC", *Nature*, Jun. 1999, vol. 399, pp. 483–487.

Tsjuimoto et al., "Bcl–2 family: Life–or–death switch", *FEBS letter*, 2000, vol. 466, pp. 6–10.

Reed et al., "Bcl–2 family proteins and mitochondria", *Biochemica et Biophysica Acta*, 1998, 1366, pp. 127–137.

Priault et al., "Investigation of bax–induced release of cytochrome c from yeast mitochondria", *Eur. J. Biochem*, 1999, 260, pp. 684–691.

\* cited by examiner

*a*

*b*

*c*

*d*

SCREENING METHOD FOR APOPTOSIS-SUPPRESSING OR-PROMOTING SUBSTANCE

This application is a national application of the 371 application of PCT/JP00/22200, filed on Apr. 05, 2000, which claims benefits of JAPAN application H11-101888, filed on Apr. 08, 1999.

TECHNICAL FIELD

The present invention relates to a screening method for substances with apoptosis (cell death)-suppressing or apoptosis-promoting activity, more particularly to a method for screening apoptosis-suppressing substance or apoptosis-promoting substance using VDAC-liposomes, or to the novel polypeptides having activities to suppress or promote apoptosis.

BACKGROUND OF THE INVENTION

Apoptosis is a cell death brought about positively by the cell per se under physiological conditions. Its morphological features are the chromatin condensation in the cell nucleus, fragmentation of the nucleus, the elimination of the cell cortical microvilli, and the condensation and fragmentation of cytoplasm. Cell cortical receptor Fas antigen triggering apoptosis, protease (caspase) indispensable for triggering apoptosis, and oncogene bcl-2 gene suppressing apoptosis, etc. have recently been demonstrated.

Oncogene bcl-2 is identified as such being activated by t(14;18) (q21;q32) chromosome translocations associated with follicular lymphoma, and is a unique oncogene displaying apoptosis-suppressing function. Various proteins that are homologous to Bcl-2 are called Bcl-2 family. Among Bcl-2 family, the presence of members with apoptosis-suppressing function represented by Bcl-2 and Bcl-$x_L$, and members with apoptosis-promoting (or inducing) function represented by Bax and Bak are known.

The followings are also known: that the mitochondria plays a crucial role in apoptotic signal transduction, and the apoptotic changes in the mitochondria are regulated by Bcl-2 family proteins; that the mitochondrial membrane potential ($\Delta\Psi$) loss and cytochrome c release are inhibited by Bcl-2 and Bcl-$x_L$ both having apoptosis-suppressing functions (Proc. Natl. Acad. Sci. USA 95, 14681–14686, 1998. J. Exp. Med. 183, 1533–1544, 1996. Cell 91 , 627–637, 1997. Proc. Natl. Acad. Sci. USA 95, 1455–1459); and that the mitochondrial membrane potential ($\Delta\Psi$) loss and cytochrome c release are induced by Bax and Bak both having apoptosis-promoting functions (Proc. Natl. Acad. Sci. USA 95, 4997–5002, 1998. J. Cell Biol. 143, 217–224, 1998. Proc. Natl. Acad. Sci. USA 95, 14681–14686, 1998).

Further known are that Bax- and Bak-dependent changes of membrane permeability are mediated by poly-protein channel called the permeability transition (referred to as PT hereinafter) pore (Proc. Natl. Acad. Sci. USA 95, 4997–5002, 1998. Proc. Natl. Acad. Sci. USA 95, 14681–14686, 1998. Science 281, 2027–2031, 1998), and that the poly-protein channel is thought to consist of VDAC (voltage-dependent anion channel) which is also called mitochondrial porin, the adenine nucleotide translocator (ANT), cyclophilin D, and some other molecules (J. Bioenerg. Biomembr. 26, 509–517, 1994. Biochem. Biophys. Acta 1241, 139–176, 1995).

VDAC is a small protein abundantly existing on the outer mitochondrial membrane, which was found to form a large (2.6 nm) voltage-dependent pore when VDAC-liposomes were formed on being incorporated by planar lipid bilayers (J. Membr. Biol. 111, 103–111, 1989). VDAC is thought to physiologically function as the pathway for various substances including ions and intermediate metabolites to get into and get from the mitochondria. Further, the present inventors have recently demonstrated that Bax and Bak interact with the PT pore (Proc. Natl. Acad. Sci. USA 95, 14681–14686, 1998. Science 281, 2027–2031, 1998). It has also been reported that Bax interacts directly with ANT (the adenine nucleotide translocator) and sensitizes ANT and PT pore-liposomes to atractyloside, i.e. an ANT ligand (Science 281, 2027–2031, 1998).

Bcl-2 and Bax are highly involved in oncogenesis. In follicular lymphoma or diffuse large cell lymphoma with t(14; 18) translocations, and in chronic lymphatic leukemia either with t(18;22)(q21;q11) or t(2;18)(q11;q21) translocations, Bcl-2 expression is deregulated by respective translocations to immunogloblin heavy chain and light chain regions, and Bcl-2 promotes suppression of cell death, contributing to oncogenesis. Meanwhile, Bax functions as a tumor-suppressor gene, suggesting its involvement in human tumor, as the mutation of Bax genes (BH1 and BH3 regions) are observed with high frequency in the tumor cell strain of blood cell system.

Bcl-2 is also deeply concerned with neurodegenerative diseases. SMN (survival motor neuron) protein is a causal gene product of spinal muscular atrophy; a genetic disease accompanied with degeneration of motor nerves and crisis of the disease is deeply associated with the decrease in Bcl-2 function due to SMN-deficiency.

The subject of the present invention is to provide the screening method for apoptosis-suppressing substance or apoptosis-promoting substance, whose future applications to pharmaceuticals or diagnostic drugs are expected since Bcl-2 family having apoptosis-suppressing or -promoting activities are deeply involved in various diseases, and to provide apoptosis-suppressing substance or apoptosis-promoting substance.

DISCLOSURE OF THE INVENTION

The present inventors have elucidated that apoptosis-suppressing function by Bcl-2, BCl-$x_L$, etc. that belong to Bcl-2 family proteins controlling apoptosis, or apoptosis-promoting function by Bax, Bak, etc. are mediated by mitochondria. They have further made a keen research on the targeting molecules and by using the liposome system, have found that Bcl-2 family proteins, directly targeting the mitochondrial outer membrane protein VDAC, regulates cytochrome c release and $\Delta\Psi$ loss that are central phenomena in apoptosis signal transduction, and thus the present invention has been accomplished.

The present invention relates to a screening method for apoptosis-suppressing substance or apoptosis-promoting substance characterized in that whether or not a subject substance has apoptosis-suppressing or—promoting activities is estimated by incubating VDAC-liposomes, an indicator substance capable of passing through VDAC, and a subject substance, and then by detecting concentration changes of a indicator substance inside or outside VDAC-liposomes before and after the incubation; a screening method for the apoptosis-suppressing substance or apoptosis-promoting substance, characterized in that the incubation is performed under the condition where an indicator substance exists in VDAC-liposomes; a screening method for the apoptosis-suppressing substance or apoptosis-promoting substance, characterized in that the incubation is performed under the condition where a subject substance exists in VDAC-liposomes; a screening method for the apoptosis-suppressing substance or apoptosis-promoting substance, characterized in that the incubation is performed under the condition where apoptosis-suppressing substance or apoptosis-promoting substance co-exists with a subject substance; a screening method for apoptosis-suppressing substance or apoptosis-promoting substance according to, characterized in that VDAC-liposomes are prepared by using recombinant human VDAC; a screening method for any of the previously described apoptosis-suppressing substance or apoptosis-promoting substance, characterized in that VDAC-liposomes are VDAC-liposomes wherein VDAC is reconstituted in a small unilamelar vesicle; a screening method for any of the previously described apoptosis-suppressing substances or apoptosis-promoting substances, characterized in that the indicator substance is a labeled compound; and a screening method for apoptosis-suppressing substances or apoptosis-promoting substances, characterized in that the labeled compound is a fluorescent-labeled cytochrome c and/or isotope-labeled sucrose.

The present invention further relates to a screening method for any of the previously described apoptosis-suppressing substances or apoptosis-promoting substances, characterized in that the subject substance is a protein or a polypeptide; a screening method for apoptosis-suppressing substances or apoptosis-promoting substances, characterized in that the protein or the polypeptide has an amino acid sequence wherein one or a few amino acids are deleted, substituted or added in amino acid sequences of Bcl-2 family proteins; a screening method for an apoptosis-suppressing substance or apoptosis-promoting substance, characterized in that the protein or the polypeptide comprises an amino acid sequence wherein one or a few amino acids are deleted, substituted or added in a polypeptide having amino acid sequence of residues 7 to 30 within the amino acid sequence shown as Seq. ID No.2 ; a screening method for apoptosis-suppressing substance or apoptosis-promoting substance, further characterized in that the protein or the polypeptide comprises an amino acid sequence wherein one or a few amino acids are deleted, substituted or added in a polypeptide having amino acid sequence of residues 4 to 23 within the amino acid sequence shown as Seq. ID No.4 ; a screening method for an apoptosis-suppressing substance or apoptosis-promoting substance, characterized in that the protein or the polypeptide comprises an amino acid sequence wherein one or a few amino acids are deleted, substituted or added in a polypeptide having amino acid sequence of residues 55 to 74 within the amino acid sequence shown as Seq. ID No.6 ; a screening method for apoptosis-suppressing substance or apoptosis-promoting substance, further characterized in that the protein or the polypeptide is obtained by using a base sequence or its complementary sequence of DNA encoding Bcl-2 family proteins and DNA including whole or part of these sequences, as a probe; a screening method for an apoptosis-suppressing substance or apoptosis-promoting substance, further characterized in that the protein or the polypeptide consists of a protein or a polypeptide obtained by using base sequence of basis 32 to 751 or its complementary sequence within the base sequence shown as Seq. ID No.1 and DNA including whole or part of these sequences, as a probe; a screening method for an apoptosis-suppressing substance or apoptosis-promoting substance, further characterized in that the protein or the polypeptide consists of a protein or a polypeptide obtained by using base sequence of basis 135 to 836 or its complementary sequence within the base sequence shown as Seq. ID No.3 and DNA including whole or part of these sequences, as a probe; and a screening method for apoptosis-suppressing substance or apoptosis-promoting substance, further characterized in that the protein or the polypeptide consists of a protein or a polypeptide obtained by using base sequence of basis 163 to 222 or its complementary sequence within the base sequence shown as Seq. ID No.5 and DNA including whole or part of these sequences, as a probe.

The present invention still further relates to a polypeptide comprising amino acid sequence of residues 7 to 30 within the amino acid sequence shown as Seq. ID No.2 ; a polypeptide with apoptosis-suppressing activity and comprising at least an amino acid sequence wherein one or a few amino acids are deleted, substituted, or added in amino acid sequence of residues 7 to 30 within the amino acid sequence shown as Seq. ID No.2 ; a polypeptide comprising amino acid sequence of residues 4 to 23 within the amino acid sequence shown as Seq. ID No.4 ; a polypeptide with apoptosis-suppressing activity and comprising at least an amino acid sequence wherein one or a few amino acids are deleted, substituted, or added in amino acid sequence of residues 4 to 23 within the amino acid sequence shown as Seq. ID No.4 ; a polypeptide comprising amino acid sequence of residues 55 to 74 within the amino acid sequence shown as Seq. ID No.6 ; a polypeptide with apoptosis-promoting activity and comprising at least an amino acid sequence wherein one or a few amino acids are deleted, substituted, or added in amino acid sequence of residues 55 to 74 within the amino acid sequence shown as Seq. ID No.6 ; a polypeptide as described above, wherein the polypeptide is chemically modified for the intracellular introduction; an apoptosis-suppressing substance obtained by any one of the screening methods described above; and an apoptosis-promoting substance obtained by any one of the screening methods described above.

THE BEST MODE TO CARRY OUT THE INVENTION

Figure 1:
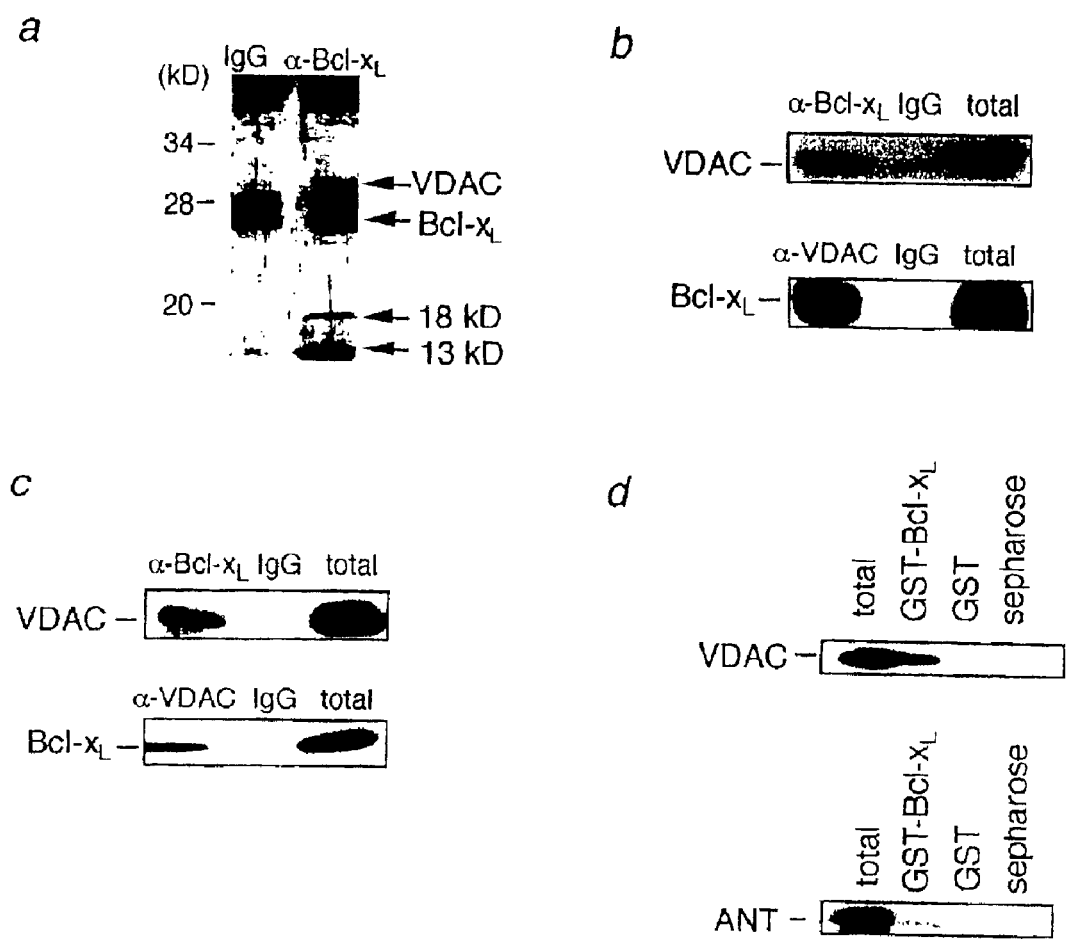
FIG. 1 shows the interaction of Bcl-$x_L$ and VDAC.

Any kind of VDAC-liposomes may be used in the present invention as long as the VDAC, also called mitochondrial porin, is embedded into lipid bilayer of liposomes which is a closed vesicle consisting of the lipid bilayer. And as VDAC which composes VDAC-liposomes, any VDAC may be used regardless of its origin, but VDAC-loposomes prepared by using human-derived-VDAC such as recombinant human VDAC is preferred to use in aspect of developing pharmaceuticals or the like. Further, as VDAC-liposomes, VDAC-liposomes wherein the VDAC is reconstituted in a small unilamelar vesicle (SUV) is preferable in view of reaction sensitivity. The conventionally known methods can be used to prepare liposomes.

As an indicator substance of the present invention, any substance will do as long as it can pass through VDAC channel such as in the presence of apoptosis-promoting substance. Still, an indicator substance easy to detect concentration changes before and after the incubation is preferable in determining whether or not the subject substance displayed apoptosis-suppressing or -promoting activities. Labeled compounds, dyes, enzymes, and the like are enumerated as indicator substances. Among them, sucrose with relatively small molecular weight which can be labeled with an isotope, and labeled cytochrome c modified with a labeled compound such as fluorescent etc. can be concretely exemplified. Release of cytochrome c is thought to be a central event in apoptotic signal transduction. Additionally, one or more than two kinds of indicator substances may be simultaneously used in the co-incubation with VDAC-liposomes, and they may be allowed to exist inside and/or outside VDAC-liposomes.

Any substance will suffice as a subject substance of the present invention as long as it is expected to be determined to see whether or not having apoptosis-suppressing or -promoting activities, and proteins that most likely have apoptosis-suppressing or -promoting activities are the concrete examples. Among the proteins, proteins consisting of whole or part of Bcl-2 family proteins already known as apoptosis-suppressing substance, or proteins wherein the polypeptides are modified/mutated, or modified/mutated polypeptides are especially preferable. The examples of modified/mutated proteins or polypeptides are proteins or polypeptides obtained by using the followings, for instance, as a probe: a protein or a polypeptide having an amino acid sequence wherein one or a few amino acids are deleted, substituted, or added within the amino acid sequence of the protein or the polypeptide; a base sequence of DNA encoding a protein or a polypeptide; or DNA including part or whole of these sequences.

Additionally, exemplified as proteins with apoptosis-suppressing activities in Bcl-2 family proteins are: Human Bcl-2 protein having the amino acid sequence shown as Seq. ID No.2, Human BCl-$x_L$ protein having the amino acid sequence shown as Seq. ID No.4, Bcl-w, Mcl-1, A1 (Bfl-1), BHRF-1 (Epstein-Barr virus), LMW-5-HL (African swine fever virus), E1B 19 kDa (Adenovirus), Ksbcl-2 (HHV8), and ORF16 (herpesvirus saimiri). Also among Bcl-2 family, exemplified as proteins having apoptosis-promoting activities are: Human Bax protein having the amino acid sequence shown as Seq ID No.6, Bcl-$x_S$, Bad, Bak, Mtd (Bok), Diva, Bik, Bid, Bim, Hrk (DP5), Blk, Bnip3, Bnip3L. Furthermore, as polypeptides consisting of a part of Bcl-2 family proteins, Bcl-2-derived polypeptide which consists of the amino acid sequence comprising amino acid sequence of residues 7 to 30 within the amino acid sequence shown as Seq. ID No.2 on the sequencing list, and Bcl-$x_L$-derived polypeptide which consists of amino acid sequence of residues 4 to 23 within the amino acid sequence shown as Seq. ID No.4 are concrete examples of polypeptides with apoptosis-suppressing activities, and Bax-derived polypeptide which consists of amino acid sequence of residues 55 to 74 within the amino acid sequence shown as Seq. ID No.6 is a concrete example having apoptosis-promoting activity, respectively.

A protein or a polypeptide obtained by using a base sequence or its complementary sequence of DNA encoding Bcl-2 family proteins and DNA including whole or part of these sequences, as a probe, may be advantageously used as a subject substance in the screening method for apoptosis-suppressing substance or -promoting substance of the present invention. The examples of DNAs coding for Bcl-2 family proteins are, for instance, DNA encoding Bcl-2 shown as Seq. ID No.1, DNA encoding Bcl-XL shown as Seq. ID No.3, and DNA encoding Bax shown as Seq. ID No.5. And the examples of a part of base sequences of DNA encoding Bcl-2 family proteins are, for instance, base sequence of basis 32 to 751 within the base sequence shown as Seq. ID No.1, base sequence of basis 135 to 836 within the base sequence shown as Seq. ID No.3, and base sequence of basis 163 to 222 within the base sequence shown as Seq. ID No.5.

In the incubation in the presence of VDAC-liposomes, a subject substance may be used alone or along with one or more than two kinds of known apoptosis-suppressing or -promoting substances. When a subject substance and apoptosis-suppressing substance is used together, apoptosis-promoting substance can be screened, and when a subject substance and apoptosis-promoting substance is used together, apoptosis-suppressing substance can be screened. Meanwhile, a substance antagonizing apoptosis-suppressing substance or a substance antagonizing apoptosis-promoting substance can also be screened. In case of the combined use, a subject substance and apoptosis-suppressing or -promoting substance are preferred to exist in VDAC-liposomes, while either or both of them may be placed outside the VDAC-liposomes. Conventionally known methods are used to make the following substances exist in VDAC-liposomes on incubation: a subject substance and apoptosis-suppressing or -promoting substance; a subject substance and an indicator substance; a subject substance and an indicator substance along with apoptosis-suppressing or -promoting substance, and the like.

Incubation conditions such as temperature, pH, reaction time, etc. will not specifically be limited in the screening method for apoptosis-suppressing or -promoting substance of the present invention. Still it is preferable to select conditions wherein the concentration changes of an indicator substance inside or outside VDAC-liposomes before and after the incubation can be detected with high sensitivity.

The present invention further relates to a polypeptide having: amino acid sequence of residues 7 to 30 within the amino acid sequence shown as Seq. ID No.2; amino acid sequence of residues 4 to 23 within the amino acid sequence shown as Seq. ID No.4; or amino acid sequence of residues 55 to 74 within the amino acid sequence shown as Seq. ID No.6. The invention still further relates to a polypeptide with apoptosis-suppressing activity, and which at least comprises an amino acid sequence wherein one or a few amino acids are deleted, substituted, or added within the following amino acid sequences: amino acid sequence of residues 7 to 30 within the amino acid sequence shown as Seq. ID No.2; amino acid sequence of residues 4 to 23 within the amino acid sequence shown as Seq. ID No.4, and amino acid sequence of residues 55 to 74 within the amino acid sequence shown as Seq. ID No.6. Still further related are, a polypeptide wherein the above peptides are chemically modified for intracellular introduction, and the apoptosis-suppressing or -promoting substances obtained by the screening method of the present invention for the screening of apoptosis-suppressing or -promoting substances. Among the sequences, amino acid sequence of residues 7 to 30 within the amino acid sequence shown as Seq. ID No.2, amino acid sequence of residues 4 to 23 within the amino acid sequence shown as Seq. ID No.4, and amino acid sequence of residues 55 to 74 within the amino acid sequence shown as Seq. ID No.6 are known respectively. Meanwhile polypeptides consisting of these amino acid sequences have never been prepared, let alone the polypeptides consisting of these amino acid sequences have never been found to act on the VDAC channel and to display apoptosis-suppressing or -promoting activities until the present invention has now displayed. For above polypeptides chemically modified for the intracellular introduction, a polypeptide can be exemplified that is attached with an oligopeptide derived from TAT, a protein produced by HIV virus, which protein makes the migration into the cell easy and smooth.

The present invention will be described in more detail with examples, but the technical scope of the invention will not be limited to these examples.

MATERIALS AND METHODS
(Antibodies)

Anti-pigeon cytochrome c monoclonal antibody (7H8.2C12) which cross-reacts with rat and horse cytochrome c, anti-yeast cytochrome c polyclonal antibody, and anti-rat ANT antibody were kindly provided by Dr. E. Margoliash (University of Illinois, IL), Dr. G. Shatz (University of Basel, Switzerland), and Dr. H. H. Schmid (University of Minessota, MN), respectively. Anti-human VDAC (porin) monoclonal antibody (31HL) which cross-reacts with rat VDAC was obtained from Calbiochem (La Jolla, Calif.). Anti-human Bcl-$x_L$ polyclonal antibody (L19) and anti-human Bax polyclonal antibody (N20) were from Santa Cruz Biotechnology (Santa Cruz, Calif.).

(Immunoprecipitation and Western blot analysis)

Rat liver mitochondria were isolated as described (Proc. Natl. Acad. Sci. USA 95, 1455–1459, 1998). Immunoprecipitation was performed as described previously (Proc. Natl. Acad. Sci. USA 95, 14681–14686) using cells and mitochondria lysed and sonicated in lysis buffer (10 mM Hepes (N-2-hydroxyethylpiperazine-N'-2-ethanesulfonic acid) pH7.4, 5 mM KCl, 5 mM $MgCl_2$, 1 mM EGTA (ethyleneglycolbis (2-aminoethylether)-tetraacetic acid), 0.5% NP40, at the final concentration) including proteinase-inhibitor. For immunoprecipitation experiments with liposomes, DTBP was used as a protein cross-linker as described previously (Mol. Cell 1, 337–346, 1998). To detect bindings between purified proteins, VDAC (0.2 μg) and ANT (0.2 μg) were incubated for 3 hours either with GST-Bcl-XL (0.2 μg) or GST (0.2 μg) in 100 μl of the lysis buffer. Subsequently these proteins were incubated with glutathione (GSH)-sepharose gel or with sepharose gel for 3 hours, and then were adsorbed. After a short-period centrifugation, gels were washed 3 times with the lysis buffer and were resuspended in the sample buffer to perform SDS (sodium dodecyl sulfate)-PAGE.

(Peptide sequencing)

Immunoprecipitates were electrophoresed on a SDS-polyacrilamide gel, and the proteins separated were excised and digested with lysil endopeptidase at 35° C. for one day. Resulting peptide fragments were separated using TSK gel (ODS-80Ts; Toso), and then directly microsequenced from N-terminal by Edman degradation for the peptide sequence to be determined.

(Protein purification)

Human Bcl-$x_L$, two kinds of BCl-$x_L$ mutants, and human Bak (lacking the C-terminal 21 residue) were expressed as GST-fusion proteins in Escherichia coli strain DH5 α and purified using a glutathione-sepharose column. The purified GST-fusion proteins were separated from GST through the function of thrombin. Human Bax was purified as a His-tagged protein as previously described (Proc. Natl. Acad. Sci. USA 95, 14681–14686). HA-tagged human VDAC1 was expressed in Escherichia coli strain DE 3 using the Xpress system (Invitrogen) and purified on a HA (dried hydroxyapatite) column. Mock control proteins were prepared using GST- or His-tagged proteins from empty vectors.

Rat liver VDAC was purified as previously described (Biochem. Biophys. Acta 905, 499–502, 1987). Briefly, rat liver mitochondria were suspended into 10 mM Tris-HCl buffer (pH7.0), 1 mM EDTA, and 3% Triton-X100 for 30 min at 0° C., and then subjected to ultracentrifugation at 37,000 g for 45 min for separation. Supernatants were added to HA and celite (9:1) column (3 g), and the first flow through a fraction (1 ml) was collected as purified VDAC protein. The purified VDAC showed a single band on the gel by SDS-polyacrylamide electrophoresis. The purity of rVDAC was shown to be >95%. Rat heart ANT was purified as described (FEBS lett. 426, 97–101, 1998). The purity of purified ANT was shown to be >90% as examined in a similar manner as the above.

(Reconstitution of VDAC in liposomes)

Purified and recombinant VDAC were reconstituted in small unilamelar vesicles by the sonic freeze-thaw procedure described previously (Biochem. Biopys. Acta 1145, 168–176, 1993) with a little alterations to the procedure. Briefly, 100mg of phospholipid (soybean, type II-S) was dissolved into 1 ml of liposome medium containing 30 mM sodium sulfonate and 20 mM Tricine-NaOH (pH7.3 or pH5.2) with or without 80 mM sucrose. After sonication, purified or recombinant VDAC protein (200 μg) was added, with or without rBcl-$x_L$ (200 μg) and rBax (200 μg), to 1 ml of phospholipid, and this suspension was subjected to two freeze-thaw cycles. Heat-denatured VDAC protein was obtained by heating at 95° C. for 10 min. Then unilamelar VDAC-liposomes were produced by mild sonication and the product was fractionated on sephadex G-50 columns. The light scatter of each fraction was measured using a spectrophotometer (UV-160A; Shimazu) at a wavelength of 520 nm, and the fraction containing 700–900 arbitrary units/μl was used in the experiments. Plain liposomes were produced by performing the same procedure without adding any protein.

A sucrose import experiment was performed by measuring $^{14}C$-sucrose uptake. Liposomes (20 μl) were incubated with 5 μl of $^{14}C$-sucrose (97%; 200 μCi/ml) at 25° C., and free $^{14}C$-sucrose were removed by centrifugation using an M.W. 30,000 limiting filter (Ultrafree-MC30,000; Millipore). Then the $^{14}C$-sucrose imported in the recovered liposomes was measured with a γ-scintilation counter (Wallac 1414).

(Cytochrome c translocation experiment)

Fluorescein isothiocyanate (referred to as FITC hereinafter)-labeled cytochrome c was prepared as described previously (Wiley Interscience.5.3.1–5.3.11, 1990). Briefly, 12 mM horse cytochrome c was dialyzed with the labeling buffer (pH9.2) containing 0.05 M borate and 0.2 M NaCl. After incubation with FITC (250 μg) for 2 hours, unbound FITC was removed by dialysis using the labeling buffer followed by Sephadex G-25 column chromatography for separation. The FITC/cytochrome c molar ratio estimated by spectrophotometer was 0.47. FITC-labeled cytochrome c was detected with a lumino image analyzer (LAS-1000; Fujifilm). Liposomes (2 μl) were incubated at pH5.2 with both sucrose (50 mM) and FITC-labeled cytochrome c (50 μM) and as variables, with rBax (1.5 μg), with rBax and rBcl-$x_L$ (both 1.5 μg), and without either in a total volume of 29 μl, and the labeled cytochrome c was visualized using confocal microphotography (LSM-745; Olympus).

The cytochrome c export experiment was performed as follows. Cytochrome c (100 μM) was mixed with liposomes (1 ml)-buffer containing sucrose (80 mM) and subjected to two cycles of freeze-thawing. After unilamerization, 20 μl of liposomes were incubated with 1 ml of sucrose-free buffer with or without 20 μg/ml of rBak for 10 min at 25° C. Then separation by centrifugation using an M.W. 30,000 limiting filter was performed to separate the liposomes from free cytochrome c. The amount of free cytochrome c was determined by the absorbance at 408 nm using a spectrophotometer, and the ratio to total cytochrome c was calculated.

(Yeast mitochondria)

VDAC-deficient yeast strain (referred to as ΔVDAC hereinafter; M22-2) and its parent strain (M3) were kind gifts from Dr. M. Forte (Vollum Institute for Advanced Biomedical Research, Oregon). A human VDAC1-expressing ΔVDAC yeast strain was produced by transfecting human vdacl cDNA using lithium acetate. Mitochondria were isolated as described previously (J. Biol. Chem. 257, 13028–13033, 1982) using 2 mg of zymolyase 20T per gram of cells to form spheroplasts. The spheroplasts were homogenized with a tight fitting homogenizer. Isolated mitochondria were suspended in 0.6M mannitol, 10 mM TrisCl (pH7.4), and 0.1% fatty acid-free BSA (referred to as yMt buffer hereinafter). Mitochondria (0.5 mg/ml) were incubated at 25° C. in yMT buffer plus 4.2 mM succinate. Δψ was assessed by measuring the uptake of rhodamine 123 (Rh 123) as described (Proc. Natl. Acad. Sci. USA 95, 1455–1459). For detection of cytochrome c release, above mitochondria were spun, and the resulting supernatants were subjected to Western blot analysis using anti-yeast cytochrome c antibodies.

[Interaction between Bcl-$x_L$ and VDAC]

(Three proteins binding to Bcl-$x_L$)

Rat liver mitochondria (1 mg/ml) was incubated for 5 min with recombinant Bcl-$x_L$ (20 μg/ml). Then the lysate of mitochondria was immunoprecipitated using either anti-Bcl-$x_L$ antibody (α-Bcl-$x_L$) or rabbit immunoglobulin G (IgG), after which the resulting immuno-complex was separated by SDS-PAGE (polyacrylamide gel) electrophoresis and was then stained by silver-staining. Three proteins, 33 kD, 18 kD, and 13 kD, binding to Bcl-$x_L$ from mitochondria were detected by co-immunoprecipitation using this anti- Bcl-XL antibody (FIG. 1a).

(Interaction between Bcl-$x_L$ and VDAC from mitochondria)

Partial amino acid sequences of the 33 kD protein obtained by the above-mentioned method matched with rat VDAC. Therefore interaction of Bcl-XL with VDAC in the isolated mitochondria were examined by Western blot analysis following the co-immunoprecipitation with anti-VDAC antibody and anti-Bcl-$x_L$ antibody. The results are shown in FIG. 1b.

(Interaction between Bcl-$x_L$ and VDAC from HepG2 cells)

Interaction between Bcl-$x_L$ and VDAC from BCl-$x_L$-expressing HepG2 cells (Oncogene 12, 2045–2050, 1996) were examined. The results are shown in FIG. 1c. Meanwhile, co-immunoprecipitable interactions of Bcl-$x_L$, with Tom40 (an endogenous outer membrane protein) and with $F_1$-ATPase (inner membrane proteins) were neither observed, indicating the specific interaction between BCl-$x_L$ and VDAC.

(Direct interaction of Bcl-$x_L$ with VDAC or with ANT)

Since the PT pore is a polyprotein channel including VDAC, co-immunoprecipitation of Bcl-$x_L$ and VDAC from the mitochondria and cells did not necessarily indicate the direct interaction between BCl-$x_L$ and VDAC. Thus the following experiment is performed to ascertain their direct interaction. Purified rat liver VDAC (0.2 μg) and rat heart ANT (0.2 μg) were incubated in the presence of either GST-Bcl-$x_L$ fusion protein (0.2 μg) or GST (0.2 μg), subsequently incubated with glutathione (GSH)-sepharose gel. VDAC and ANT that had been incubated with GST-Bcl-$x_L$ were also incubated with sepharose gel. Then the gel was washed three times and bound VDAC and ANT were detected by Western blot analysis. The results are shown in FIG. 1d. In FIG. 1d, "total" indicates the amount of each protein used for immunoprecipitation. As shown in FIG. 1d, VDAC purified from rat liver mitochondria efficiently bound to GST- Bcl-$x_L$-fusion protein, indicating that BCl-$x_L$ interacted directly with VDAC. Meanwhile, ANT purified from rat heart showed only low level binding to GST-Bcl-$x_L$, which was consistent with the previous observation (Science 281, 2027–2031, 1998).

[Inhibition of VDAC activity by Bcl-$x_L$ in VDAC-liposomes]

(Sucrose uptake by VDAC-liposome)

Figure 2:
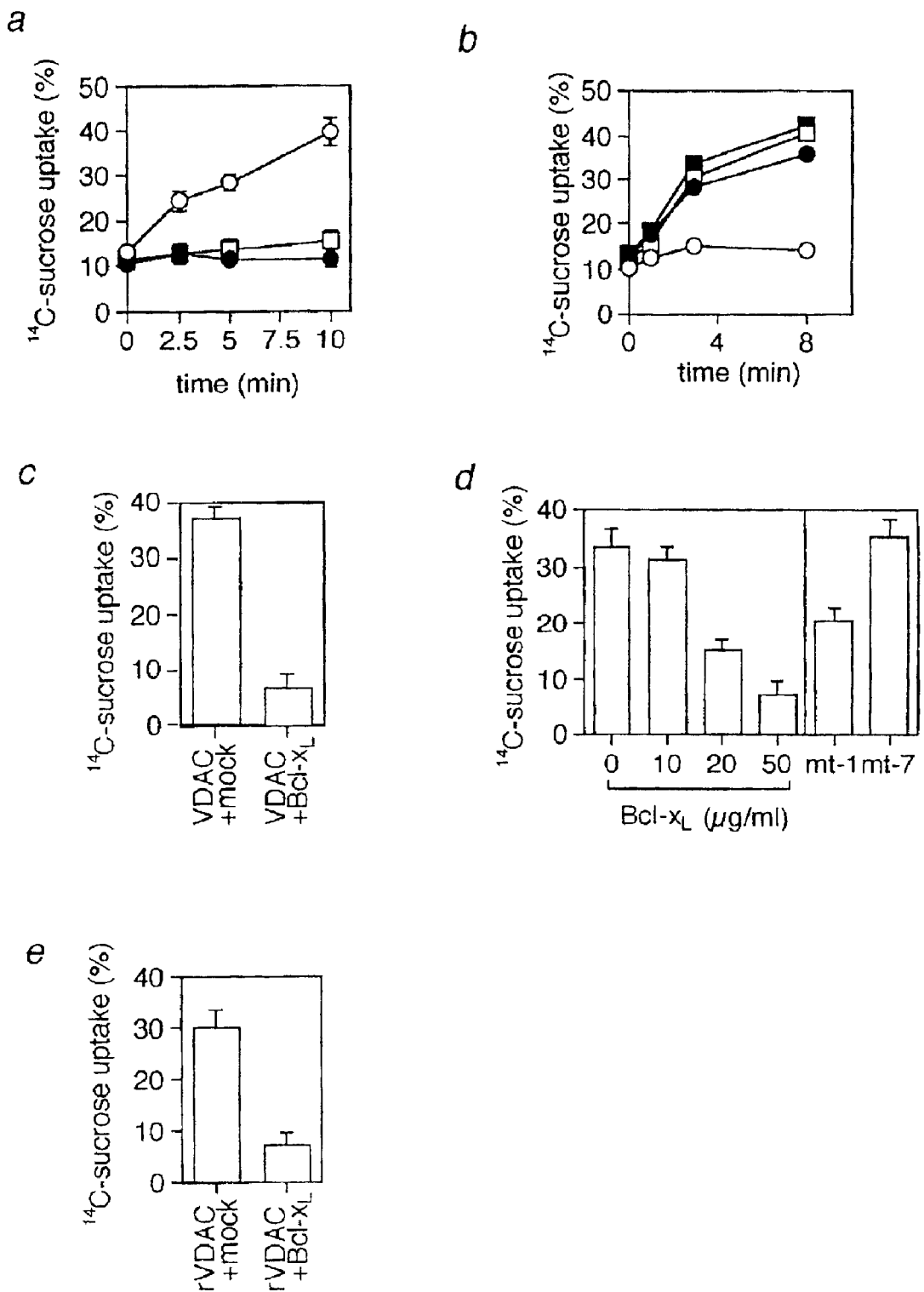
FIG. 2 shows the inhibition of VDAC activity by Bcl-$x_L$ in the VDAC-liposomes system.

The direct interaction between Bcl-$x_L$ and VDAC was confirmed in the above experiment. Whether Bcl-$x_L$ directly modulates VDAC activity was subsequently examined. VDAC purified from rat liver mitochondria homogenate was reconstituted in liposomes. Other than this VDAC-liposomes, heat-denatured VDAC-liposomes as well as plain liposomes for control were used. Each of these liposomes was incubated with $^{14}$C sucrose (1 μCi) at pH5.2 for a given period. After having been filtered by centrifugation using an M.W. 30,000 limiting filter, liposomes were collected and lysed in 2% SDS and the radiation of $^{14}$C sucrose in the liposomes were determined. The results are shown in FIG. 2a. As seen from FIG. 2a, unlike heat-denatured VDAC-liposomes (□-□) or plain liposomes (●-●), VDAC-liposomes (○-○) incorporated isotope-labeled sucrose, suggesting the sucrose uptake by liposomes was mediated by VDAC.

(Inhibition of VDAC activity in VDAC-liposomes by Bcl-$x_L$)

VDAC-liposomes were incubated at pH5.2 with 20 μg/ml of recombinant Bcl-$x_L$ (○-○) or mock protein (●-●) respectively, together with $^{14}$C sucrose (1 μCi). Likewise, plain liposomes were also incubated either with recombinant Bcl-$x_L$ (□-□) or with mock protein (■-■) at pH7.3. These results are shown in FIG. 2b. VDAC-mediated sucrose uptake was inhibited when Bcl-$x_L$ was added at pH5.2. The fact that Bcl-$x_L$ functioned in acid pH was consistent with observations previously described (Science 277, 370–372, 1997. Nature385, 353–357, 1997. Proc. Natl. Acad. Sci. USA 94, 5113–5118, 1997. Proc. Natl. Acad. Sci. USA 94, 11357–11362, 1997) that r Bc$^1$-$x_L$ acted as an ion channel on synthetic lipid membranes only under acidic conditions. Next, simultaneous insertion of Bcl-$x_L$ and VDAC into liposomes was examined.

(Inhibition of VDAC activity by Bcl-$x_L$ under neutral pH in liposomes including VDAC and recombinant Bcl-$x_L$)

VDAC/ Bcl-$x_L$ liposomes and VDAC/mock protein liposomes, into which purified VDAC and either recombinant Bcl-$x_L$ or mock protein was simultaneously inserted into liposomes were incubated at pH7.3 for 3 min with $^{14}$C sucrose (1 μCi), then $^{14}$C sucrose uptake was measured. The results are shown in FIG. 2c. As shown in FIG. 2c, Bcl-$x_L$ could function to inhibit $^{14}$C sucrose uptake even at a pH of 7.3, suggesting that the acid environment facilitated incorporation of Bcl-$x_L$ itself into liposomes. VDAC has been reported to close at a pH of below 5.0, whereas VDAC-liposomes of the present invention also did not show any significant difference in behavior between pH5.2 and pH7.3.

(Inhibitory effect on VDAC activity by various doses of Bcl-$x_L$ and by Bcl-$x_L$ mutants)

VDAC-liposomes were incubated at pH5.2 for 3 min with 0, 10, 20, or 50 µg/ml of recombinant Bcl-$x_L$ or 20 µg/ml of recombinant Bcl-$x_L$ mutants mt-1 (F131V, D133A) and mt-7 (135–137 correspond to AIL to VNW) in the presence of $^{14}$C sucrose (1 µCi). Subsequently $^{14}$C sucrose in the liposomes was measured. The results are shown in FIG. 2d. As seen from FIG. 2d, inhibition on VDAC activity increases as recombinant Bcl-x dose increases. It has previously been described that among two recombinant Bcl-$x_L$ mutants, mt-1 has partial anti-apoptic activity and mt-7 has no anti-apoptic activity at all (Nature 379, 554–556, 1996). Whereas mt-1 has a partial inhibiting function and mt-7 has no inhibiting function at all respectively on VDAC-mediated sucrose uptake. These reveal the correlation between the two activities.

(Inhibition of VDAC activity by Bcl-$x_L$ in liposomes incorporated with recombinant VDAC)

Purified recombinant VDAC was incorporated into liposomes followed by incubation with $^{14}$C sucrose (1 µCi) and recombinant Bcl-$x_L$ (20 µg/ml) at pH5.2 for 3 min, and $^{14}$C sucrose uptake was measured. The results are shown in FIG. 2e. When VDAC-liposomes were produced using recombinant VDAC, inhibition of VDAC activity by Bcl-$x_L$ was also observed, so that VDAC was confirmed to be the direct target of Bcl-$x_L$.

[Inhibition of VDAC activity by rBcl-$x_L$ and enhancement of VDAC activity by rBax]

Whether Bax affects VDAC activity was next examined.

(Enhancement of $^{14}$C sucrose uptake into VDAC-liposomes by Bax)

Figure 3:
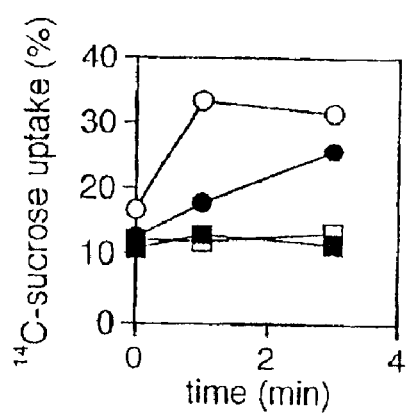
FIG. 3 shows the enhancement of VDAC activity by rBax and the inhibition of VDAC activity by rBcl-$x_L$.
Figure 3:
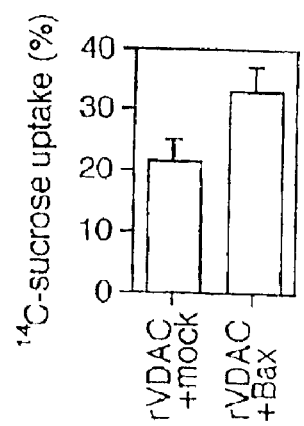
Figure 3:
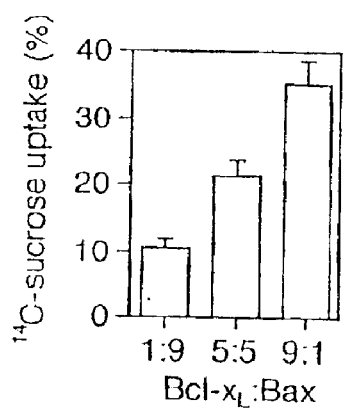
Figure 3:
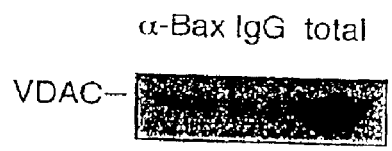

VDAC-liposomes were incubated for a given period at pH5.2 using $^{14}$C sucrose (1 µCi), with 20 µg/ml of recombinant Bax (○-○) or with mock protein (●-●). Likewise, VDAC-liposomes was converted to plain liposomes and was then incubated with recombinant Bax (□-□) or with mock protein (■-■). Liposomes were filtered by centrifugation using M.W. 30,000 limiting filter. Liposomes were then collected and lysed in 2% SDS, then radioactivity of $^{14}$C sucrose in the liposomes were measured. The results are shown in FIG. 3a. As seen in FIG. 3a, VDAC-mediated sucrose uptake was increased by rBax, while sucrose uptake in plain liposomes by uptake of Bax itself was not observed. This demonstrates the increase of rBax-induced sucrose uptake was not mediated by Bax ion channel but via some effect of Bax on VDAC.

(Enhancement of VDAC activity by Bax in liposomes into which recombinant VDAC was incorporated)

Purified recombinant VDAC was incorporated into liposomes and was incubated either with recombinant Bax (20 µg/ml) or with mock protein in the presence of $^{14}$C sucrose (1 µCi) at pH5.2. Then $^{14}$C sucrose uptake was determined for 3 min. The results are shown in FIG. 3b. As is understood from FIG. 3b, similar results were observed when VDAC-liposomes were prepared with recombinant VDAC.

(Counteraction concerning sucrose import into VDAC-liposomes by rBax and rBcl-$x_L$)

Incubation at pH5.2 using $^{14}$C sucrose (1 µCi) and VDAC-liposomes with rBax and rBcl-$x_L$ at the ratios shown in FIG. 3c, and $^{14}$C sucrose uptake was determined for 3 min. The results are shown in FIG. 3c. As shown in FIG. 3c, rBax and Bcl-$x_L$ showed counteraction on VDAC activity.

(Direct interaction of Bax and VDAC)

When rBax and VDAC are incorporated into liposomes together, Bax displayed apoptosis-promoting activity at the pH of 7.3. A similar result was obtained when a mutant deficient of C-terminal 21 residue of Bak, having apoptosis-promoting activity, was used instead of rBax. Western blot analysis of the immuno-complex using anti-VDAC antibodies revealed that VDAC prepared from rat liver and *Escherichia coli* contain no ANT of detectable level, and thus sucrose uptake by VDAC-liposomes was not affected by two kinds of ligands, i.e. atractyloside and bongkrekic acid. It can be thus concluded that the VDAC preparation was not contaminated with ANT.

[Induction of cytochrome c passing through VDAC by Bax and Bak]

The present inventors have previously described that Bax and Bak induce cytochrome c release in isolated mitochondria (Proc. Natl. acad. Sci. USA 95, 4997–5002, 1998. J. Cell Biol. 143, 217–224, 1998. Proc. Natl. acad. Sci. USA 95, 14681–14686, 1998) via PT pore (Proc. Natl. acad. Sci. USA 95, 4997–5002, 1998. Proc. Natl. acad. Sci. USA 95, 14681–14686, 1998). As aforementioned, it is now clear that Bax and Bak directly increase VDAC activity. Therefore, whether cytochrome c is released via VDAC in the presence of Bax and Bak was next examined.

(FITC-labeling of cytochrome c)

Figure 4:
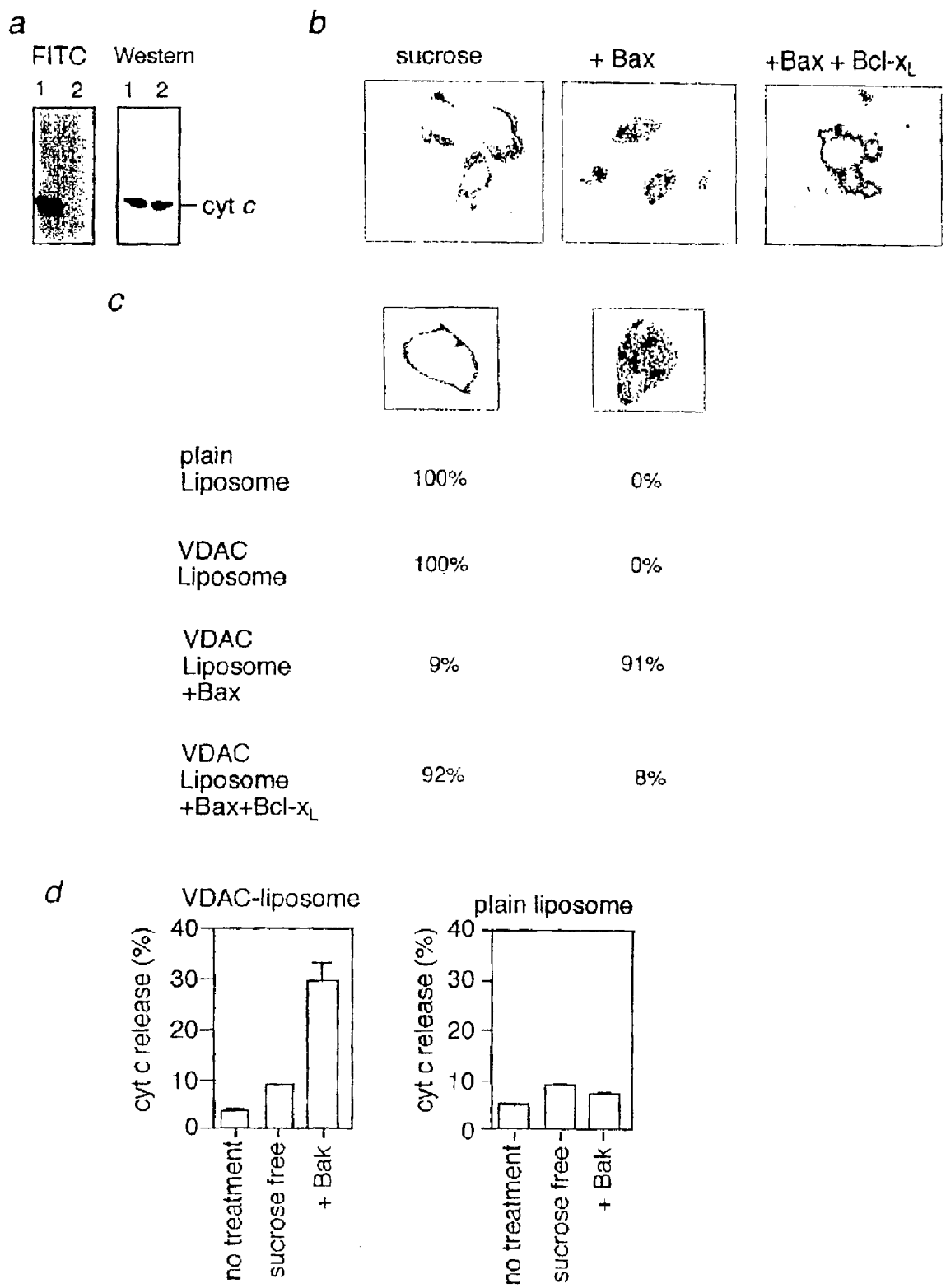
FIG. 4 shows that Bax and Bak induce passing of cytochrome c through VDAC.

In order to microscopically determine the migration of cytochrome C, FITC-labeled cytochrome c was prepared in a manner as not to largely alter its molecular weight, and was then analyzed by SDS-polyacrilamide gel electorphoresis. FITC was detected by fluorescence and cytochrome c was detected by Western blot analysis using anti-cytochrome c antibodies, respectively. In FIG. 4a, Lane 1 indicates FITC-cytochrome c (25 pg), and Lane 2 indicates cytochrome c (25 pg), respectively.

(FITC-cytochrome c uptake into VDAC-liposomes induced by Bax)

As mentioned above, VDAC-liposomes (FIGS. 4b, 4c) and plain liposomes (FIG. 4c) were incubated for 5 min at pH5.2 in the presence of 50 µM FITC-cytochrome c and 50 mM sucrose, together with rBax (52 µg/ml), with both rBax and rBcl-$x_L$ (52 µg/ml each), or with neither, followed by observation using a confocal fluorescent microscope. FIG. 4b shows typical photographs (×4, 800) of VDAC-liposomes. Liposomes were classified according to the accumulation of cytochrome c in liposomes. The frequency (%) and the typical photographs are shown in FIG. 4c. The photos are both 2 µm×2 µm.

Detection of labeled cytochrome c under a confocal fluorescent microscope, following the incubation of VDAC-liposomes using FITC-labeled cytochrome c in the presence of sucrose as shown in FIG. 4b or 4c, revealed the accumulation of cytochrome c on the plain liposome surface as well as VDAC-liposomes in the absence of rBax (FIG. 4b,4c). Contrarily, the accumulation of cytochrome c was observed inside VDAC-liposomes in the presence of rBax (FIG. 4b, 4c), suggesting that Bax allows cytochrome c to pass through VDAC. In the co-presence of rBax and rBcl-$x_L$, Bax-mediated migration of cytochrome c was inhibited (FIG. 4b, 4c). Similar results were obtained by using Bak instead of rBax.

(Bak-induced cytochrome c release from VDAC-liposomes)

As described above, VDAC-liposomes (left panel) and plain liposomes (right panel) containing 80 mM sucrose and 100 µM cytochrome c were incubated in sucrose-free buffer for 5 min at pH5.2, in the presence or absence of rBak (20 µg/ml). The results are shown in FIG. 4d. In FIG. 4d, whole amount of cytochrome c first incorporated is indicated as 100%. Additionally, cytochrome c release was determined by a spectrophotometer.

As understood from FIG. 4d, when VDAC-liposomes were incubated first by incorporating cytochrome c and sucrose into VDAC-liposomes and then by using sucrose-free buffer, cytochrome c was largely released in the presence of rBak. Whereas such cytochrome c release was not observed when plain liposomes were used in the presence of rBax. Further, after the incubation in sucrose-free buffer, a small amount of cytochrome c release was observed both in VDAC-liposomes and in plain liposomes. This is thought because cytochrome c, non-specifically bound to the surface of liposomes, was liberated.

Cytochrome c was observed to pass through VDAC by Bak also in the absence of sucrose. The number of liposomes remain unchanged during these experiments as determined by flowcytometry. On adding rBak to VDAC-liposomes including GST-green fluorescent protein (GFP), GST-GFP fusion protein (50 kD) was not released, suggesting that liposomes were not disrupted. Additionally, when rBax was used in place of rBak, similar passage of cytochrome c through VDAC was observed.

[VDAC requirement for Bak-induced $\Delta\psi$ loss and cytochrome c release in yeast mitochondria]

Since Bcl-2 family proteins were found to directly target VDAC in order to mediate channel activity, next examined was whether VDAC was targeted by Bcl-2 family proteins that are involved in the regulation of apoptosis-associated mitochondrial $\Delta\Psi$ loss and cytochrome c release.

(Inability of VDAC-deficient mitochondria for rBak-induced $\Delta\Psi$ loss)

$\Delta$VDAC which is deficient of VDAC1 (Science 247, 1233–1236, 1990) was used for the following reasons. Firstly, mammalian VDAC-deficient cells are unavailable, and secondly Bcl-2 family proteins are found to function in yeast cells (FEBS lett. 380, 169–175, 1996. Molecular Cell 1, 327–336, 1998). Mitochondria (0.5 mg/ml), isolated respectively from wild yeast, $\Delta$VDAC and $\Delta$VDAC yeast expressing human VDAC (hVDAC), were incubated in the presence of Rh123, using rBak (50 μg/ml) (FIG. 5a), mock protein (50 μg/ml) (FIG. 5b), or both rBak (50 μg/ml) and rBcl-$x_L$ (20 μg/ml) (FIG. 5c), and $\Delta\Psi$ was determined. The results are shown in FIGS. 5a–c.

(VDAC1-deficient mitochondria not showing Bak-induced cytochrome c release)

Mitochondria (0.5mg/ml), isolated from wild yeast, $\Delta$VDAC or hVDAC-expressing $\Delta$VDAC yeast (hVDAC), were incubated for 20 min using either rBak (50 μg/ml) or mock protein (50 μg/ml) in the presence or absence of rBcl-$x_L$ (20 μg/ml). The samples were centrifugated and a part of the supernatant (20 μl) was analyzed by Western blot method using anti-yeast cytochrome c antibodies. The results are shown in FIG. 5d. "Total" in FIG. 5d indicates mitochondria of the equivalent volume.

Figure 5:
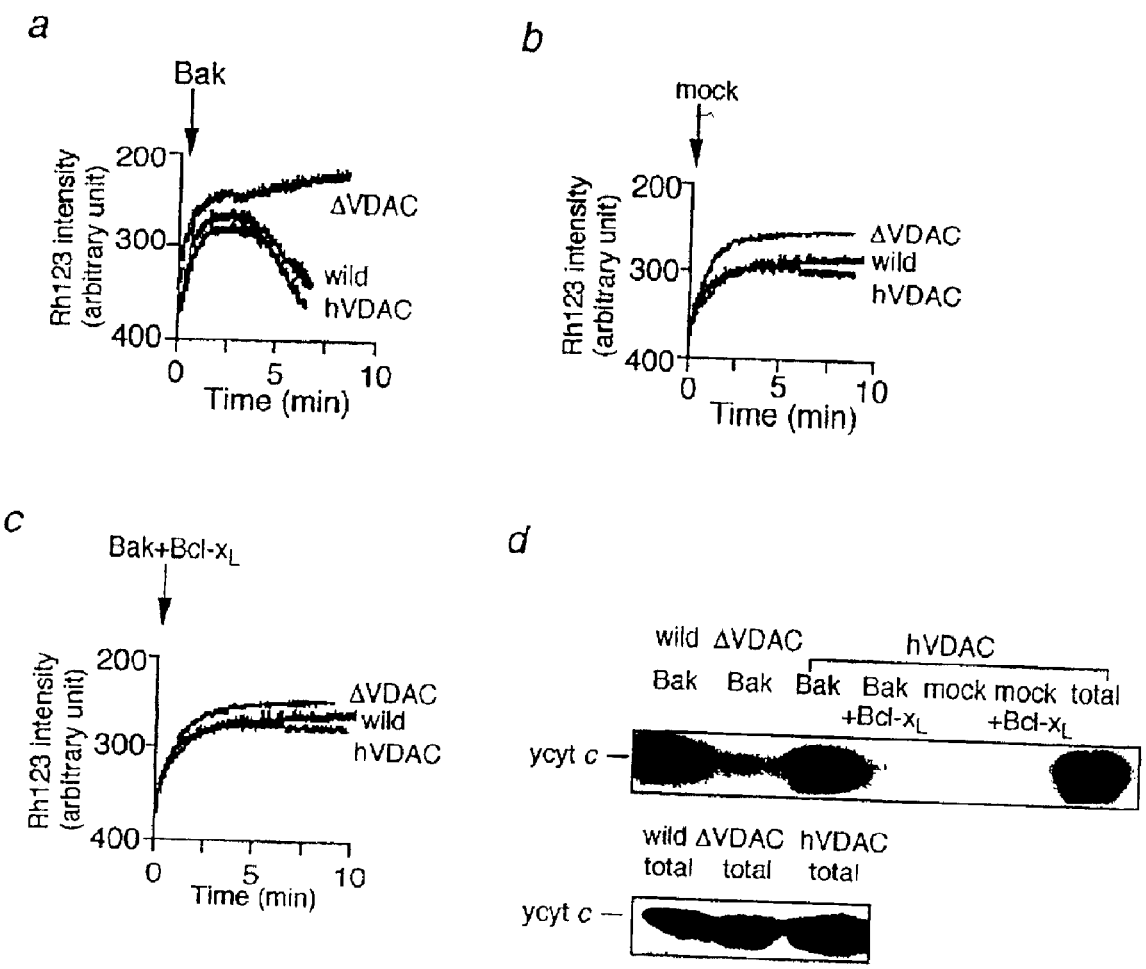
FIG. 5 shows the requirement of VDAC for Bak-induced $\Delta\Psi$ loss and cytochrome c release in yeast mitochondria.

As is obvious from FIGS. 5a and 5d, mitochondria isolated from wild yeast, as well as mammalian mitochondria, showed $\Delta\Psi$ loss and cytochrome c release on addition of rBak. On the other hand, mitochondria isolated from $\Delta$VDAC yeast did not show $\Delta\Psi$ loss and cytochrome c release by rBax. Meanwhile, in mitochondria isolated from $\Delta$VDAC yeast which was transfected with human vdacl gene (hVDAC), rBak induced $\Delta\Psi$ loss and cytochrome c release. From this, non-responsiveness of mitochondria isolated from $\Delta$VDAC yeast to rBak was thought to be due to absence of functional VDAC.

As shown in FIGS. 5c and 5d, Bak-mediated $\Delta\Psi$ loss and cytochrome c release were inhibited by Bcl-$x_L$ in yeast mitochondria. The possibility that the quality difference in mitochondria used would affect the experimental results was excluded since mitochondria used in the present invention all had the same level of ATP. The above results thus clarify that Bcl-2 family proteins target VDAC and regulate $\Delta\Psi$ loss and cytochrome c release of apoptosis-associated mitochondria.

INDUSTRIAL APPLICABILITY

The screening method for apoptosis-inhibiting substance or apoptosis-promoting substance of the present invention enables to provide apoptosis-inhibiting or apoptosis-promoting substance whose applications to pharmaceuticals and diagnostic drugs for diseases caused by apoptosis-inhibiting or -promoting activities are expected. Additionally, applications of apoptosis-inhibiting or -promoting substances of the present invention to the pharmaceuticals and diagnostic drugs used for diseases caused by apoptosis-inhibiting or -promoting activities are expectable.

What is claimed:

1. An in vitro screening method for an apoptosis-suppressing substance, wherein concentration changes of the indicator substance indicate that the test substance would suppress apoptosis, comprising determining whether or not a test substance has apoptosis-suppressing activities comprising incubating voltage-dependent anion channel-liposomes, an indicator substance selected from the group consisting of label compound, dyes and enzymes and capable of passing through voltage-dependent anion, and a test substance selected from the group consisting of proteins or polypeptides, and then detecting concentration changes of a indicator substance inside or outside voltage-dependent anion channel-liposomes before and after the incubation.

2. A screening method for apoptosis-suppressing substance according to claim 1, wherein the incubation is performed under the condition where the indicator substance exists inside the voltage-dependent anion channel-liposomes.

3. A screening method for apoptosis-suppressing substance according to claim 1, wherein the incubation is performed under the condition where the test substance selected from the group consisting of proteins or polypeptides exists inside the voltage-dependent anion channel-liposomes.

4. A screening method for apoptosis-suppressing substance according to claim 1, wherein the voltage-dependent anion channel-liposomes are prepared by using recombinant human voltage-dependant anion channel.

5. A screening method for apoptosis-suppressing substance according to claim 1, wherein voltage-dependant anion channel-liposomes are voltage dependant anion channel-liposomes wherein a voltage-dependant anion channel is reconstituted in a small unilamelar vesicle.

6. A screening method for apoptosis-suppressing substance according to claim 1, wherein the indicator substance is a labeled compound.

7. A screening method for apoptosis-suppressing substance according to claim 6, wherein the labeled compound is fluorescent-labeled cytochrome c and/or isotope-labeled sucrose.

* * * * *

SEQUENCE LISTING

```
<160> NUMBER OF SEQ ID NOS: 6

<210> SEQ ID NO 1
<211> LENGTH: 771
<212> TYPE: DNA
<213> ORGANISM: Homo sapiens
<220> FEATURE:
<221> NAME/KEY: CDS
<222> LOCATION: (32)..(751)
<223> OTHER INFORMATION: Human Bcl-2 protein

<400> SEQUENCE: 1
gttggccccc gttactttc ctctgggaaa t atg gcg cac gct ggg aga aca        52
                                  Met Ala His Ala Gly Arg Thr
                                    1               5 ggg tac gat aac cgg gag ata gtg atg aag tac atc cat tat aag ctg      100
Gly Tyr Asp Asn Arg Glu Ile Val Met Lys Tyr Ile His Tyr Lys Leu
        10                  15                  20 tcg cag agg ggc tac gag tgg gat gcg gga gat gtg ggc gcc gcg ccc      148
```

```
Ser Gln Arg Gly Tyr Glu Trp Asp Ala Gly Asp Val Gly Ala Ala Pro
        25                  30                  35 ccg ggg gcc gcc ccc gcg ccg ggc atc ttc tcc tcg cag ccc ggg cac    196
Pro Gly Ala Ala Pro Ala Pro Gly Ile Phe Ser Ser Gln Pro Gly His
 40                  45                  50                  55 acg ccc cat aca gcc gca tcc cgg gac ccg gtc gcc agg acc tcg ccg    244
Thr Pro His Thr Ala Ala Ser Arg Asp Pro Val Ala Arg Thr Ser Pro
                 60                  65                  70 ctg cag acc ccg gct gcc ccc ggc gcc gcc gcg ggg cct gcg ctc agc    292
Leu Gln Thr Pro Ala Ala Pro Gly Ala Ala Ala Gly Pro Ala Leu Ser
                 75                  80                  85 ccg gtg cca cct gtg gtc cac ctg acc ctc cgc cag gcc ggc gac gac    340
Pro Val Pro Pro Val Val His Leu Thr Leu Arg Gln Ala Gly Asp Asp
         90                  95                 100 ttc tcc cgc cgc tac cgc cgc gac ttc gcc gag atg tcc agg cag ctg    388
Phe Ser Arg Arg Tyr Arg Arg Asp Phe Ala Glu Met Ser Arg Gln Leu
        105                 110                 115 cac ctg acg ccc ttc acc gcg cgg gga cgc ttt gcc acg gtg gtg gag    436
His Leu Thr Pro Phe Thr Ala Arg Gly Arg Phe Ala Thr Val Val Glu
120                 125                 130                 135 gag ctc ttc agg gac ggg gtg aac tgg ggg agg att gtg gcc ttc ttt    484
Glu Leu Phe Arg Asp Gly Val Asn Trp Gly Arg Ile Val Ala Phe Phe
                140                 145                 150 gag ttc ggt ggg gtc atg tgt gtg gag agc gtc aac cgg gag atg tcg    532
Glu Phe Gly Gly Val Met Cys Val Glu Ser Val Asn Arg Glu Met Ser
            155                 160                 165 ccc ctg gtg gac aac atc gcc ctg tgg atg act gag tac ctg aac cgg    580
Pro Leu Val Asp Asn Ile Ala Leu Trp Met Thr Glu Tyr Leu Asn Arg
        170                 175                 180 cac ctg cac acc tgg atc cag gat aac gga ggc tgg gat gcc ttt gtg    628
His Leu His Thr Trp Ile Gln Asp Asn Gly Gly Trp Asp Ala Phe Val
    185                 190                 195 gaa ctg tac ggc ccc agc atg cgg cct ctg ttt gat ttc tcc tgg ctg    676
Glu Leu Tyr Gly Pro Ser Met Arg Pro Leu Phe Asp Phe Ser Trp Leu
200                 205                 210                 215 tct ctg aag act ctg ctc agt ttg gcc ctg gtg gga gct tgc atc acc    724
Ser Leu Lys Thr Leu Leu Ser Leu Ala Leu Val Gly Ala Cys Ile Thr
                220                 225                 230 ctg ggt gcc tat ctg ggc cac aag tga agtcaacatg cctgccccaa          771
Leu Gly Ala Tyr Leu Gly His Lys
            235                 240

<210> SEQ ID NO 2
<211> LENGTH: 239
<212> TYPE: PRT
<213> ORGANISM: Homo sapiens

<400> SEQUENCE: 2

Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
                20                  25                  30

Gly Asp Val Gly Ala Ala Pro Gly Ala Ala Pro Ala Pro Gly Ile
             35                  40                  45

Phe Ser Ser Gln Pro Gly His Thr Pro His Thr Ala Ala Ser Arg Asp
         50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Pro Val Val His Leu Thr
```

-continued

```
                        85                  90                  95
Leu Arg Gln Ala Gly Asp Asp Phe Ser Arg Arg Tyr Arg Arg Asp Phe
            100                 105                 110
Ala Glu Met Ser Arg Gln Leu His Leu Thr Pro Phe Thr Ala Arg Gly
            115                 120                 125
Arg Phe Ala Thr Val Val Glu Glu Leu Phe Arg Asp Gly Val Asn Trp
            130                 135                 140
Gly Arg Ile Val Ala Phe Phe Glu Phe Gly Gly Val Met Cys Val Glu
145                 150                 155                 160
Ser Val Asn Arg Glu Met Ser Pro Leu Val Asp Asn Ile Ala Leu Trp
                165                 170                 175
Met Thr Glu Tyr Leu Asn Arg His Leu His Thr Trp Ile Gln Asp Asn
            180                 185                 190
Gly Gly Trp Asp Ala Phe Val Glu Leu Tyr Gly Pro Ser Met Arg Pro
            195                 200                 205
Leu Phe Asp Phe Ser Trp Leu Ser Leu Lys Thr Leu Leu Ser Leu Ala
210                 215                 220
Leu Val Gly Ala Cys Ile Thr Leu Gly Ala Tyr Leu Gly His Lys
225                 230                 235

<210> SEQ ID NO 3
<211> LENGTH: 926
<212> TYPE: DNA
<213> ORGANISM: Homo sapiens
<220> FEATURE:
<221> NAME/KEY: CDS
<222> LOCATION: (135)..(836)
<223> OTHER INFORMATION: Human Bcl-xL protein

<400> SEQUENCE: 3
gaatctcttt ctctcccttc agaatcttat cttggctttg gatcttagaa gagaatcact      60
aaccagagac gagactcagt gagtgagcag gtgttttgga caatggactg gttgagccca     120
tccctattat aaaa atg tct cag agc aac cgg gag ctg gtg gtt gac ttt       170
              Met Ser Gln Ser Asn Arg Glu Leu Val Val Asp Phe
                1               5                  10 ctc tcc tac aag ctt tcc cag aaa gga tac agc tgg agt cag ttt agt       218
Leu Ser Tyr Lys Leu Ser Gln Lys Gly Tyr Ser Trp Ser Gln Phe Ser
            15                  20                  25 gat gtg gaa gag aac agg act gag gcc cca gaa ggg act gaa tcg gag       266
Asp Val Glu Glu Asn Arg Thr Glu Ala Pro Glu Gly Thr Glu Ser Glu
     30                  35                  40 atg gag acc ccc agt gcc atc aat ggc aac cca tcc tgg cac ctg gca       314
Met Glu Thr Pro Ser Ala Ile Asn Gly Asn Pro Ser Trp His Leu Ala
45                  50                  55                  60 gac agc ccc gcg gtg aat gga gcc act gcg cac agc agc agt ttg gat       362
Asp Ser Pro Ala Val Asn Gly Ala Thr Ala His Ser Ser Ser Leu Asp
            65                  70                  75 gcc cgg gag gtg atc ccc atg gca gca gta aag caa gcg ctg agg gag       410
Ala Arg Glu Val Ile Pro Met Ala Ala Val Lys Gln Ala Leu Arg Glu
         80                  85                  90 gca ggc gac gag ttt gaa ctg cgg tac cgg cgg gca ttc agt gac ctg       458
Ala Gly Asp Glu Phe Glu Leu Arg Tyr Arg Arg Ala Phe Ser Asp Leu
     95                 100                 105 aca tcc cag ctc cac atc acc cca ggg aca gca tat cag agc ttt gaa       506
Thr Ser Gln Leu His Ile Thr Pro Gly Thr Ala Tyr Gln Ser Phe Glu
110                 115                 120 cag gta gtg aat gaa ctc ttc cgg gat ggg gta aac tgg ggt cgc att       554
Gln Val Val Asn Glu Leu Phe Arg Asp Gly Val Asn Trp Gly Arg Ile
            125                 130                 135
```

-continued

```
                  125                 130                 135                 140
gtg gcc ttt ttc tcc ttc ggc ggg gca ctg tgc gtg gaa agc gta gac         602
Val Ala Phe Phe Ser Phe Gly Gly Ala Leu Cys Val Glu Ser Val Asp
                145                 150                 155 aag gag atg cag gta ttg gtg agt cgg atc gca gct tgg atg gcc act         650
Lys Glu Met Gln Val Leu Val Ser Arg Ile Ala Ala Trp Met Ala Thr
        160                 165                 170 tac ctg aat gac cac cta gag cct tgg atc cag gag aac ggc ggc tgg         698
Tyr Leu Asn Asp His Leu Glu Pro Trp Ile Gln Glu Asn Gly Gly Trp
                175                 180                 185 gat act ttt gtg gaa ctc tat ggg aac aat gca gca gcc gag agc cga         746
Asp Thr Phe Val Glu Leu Tyr Gly Asn Asn Ala Ala Ala Glu Ser Arg
        190                 195                 200 aag ggc cag gaa cgc ttc aac cgc tgg ttc ctg acg ggc atg act gtg         794
Lys Gly Gln Glu Arg Phe Asn Arg Trp Phe Leu Thr Gly Met Thr Val
205                 210                 215                 220 gcc ggc gtg gtt ctg ctg ggc tca ctc ttc agt cgg aaa tga                 836
Ala Gly Val Val Leu Leu Gly Ser Leu Phe Ser Arg Lys
                225                 230 ccagacactg accatccact ctaccctccc acccccttct ctgctccacc acatcctccg       896
tccagccgcc attgccacca ggagaacccg                                        926
```

<210> SEQ ID NO 4
<211> LENGTH: 233
<212> TYPE: PRT
<213> ORGANISM: Homo sapiens

<400> SEQUENCE: 4

```
Met Ser Gln Ser Asn Arg Glu Leu Val Val Asp Phe Leu Ser Tyr Lys
  1               5                  10                  15

Leu Ser Gln Lys Gly Tyr Ser Trp Ser Gln Phe Ser Asp Val Glu Glu
                 20                  25                  30

Asn Arg Thr Glu Ala Pro Glu Gly Thr Glu Ser Glu Met Glu Thr Pro
             35                  40                  45

Ser Ala Ile Asn Gly Asn Pro Ser Trp His Leu Ala Asp Ser Pro Ala
         50                  55                  60

Val Asn Gly Ala Thr Ala His Ser Ser Ser Leu Asp Ala Arg Glu Val
 65                  70                  75                  80

Ile Pro Met Ala Ala Val Lys Gln Ala Leu Arg Glu Ala Gly Asp Glu
                 85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220
```

Leu Leu Gly Ser Leu Phe Ser Arg Lys
225                 230

<210> SEQ ID NO 5
<211> LENGTH: 579
<212> TYPE: DNA
<213> ORGANISM: Homo sapiens
<220> FEATURE:
<221> NAME/KEY: CDS
<222> LOCATION: (1)..(579)
<223> OTHER INFORMATION: Human Bax protein

<400> SEQUENCE: 5

| | | |
|---|---|---|
| atg gac ggg tcc ggg gag cag ccc aga ggc ggg ggg ccc acc agc tct<br>Met Asp Gly Ser Gly Glu Gln Pro Arg Gly Gly Gly Pro Thr Ser Ser<br>1               5                   10                  15 | | 48 |
| gag cag atc atg aag aca ggg gcc ctt ttg ctt cag ggt ttc atc cag<br>Glu Gln Ile Met Lys Thr Gly Ala Leu Leu Leu Gln Gly Phe Ile Gln<br>            20                  25                  30 | | 96 |
| gat cga gca ggg cga atg ggg ggg gag gca ccc gag ctg gcc ctg gac<br>Asp Arg Ala Gly Arg Met Gly Gly Glu Ala Pro Glu Leu Ala Leu Asp<br>        35                  40                  45 | | 144 |
| ccg gtg cct cag gat gcg tcc acc aag aag ctg agc gag tgt ctc aag<br>Pro Val Pro Gln Asp Ala Ser Thr Lys Lys Leu Ser Glu Cys Leu Lys<br>50                  55                  60 | | 192 |
| cgc atc ggg gac gaa ctg gac agt aac atg gag ctg cag agg atg att<br>Arg Ile Gly Asp Glu Leu Asp Ser Asn Met Glu Leu Gln Arg Met Ile<br>65                  70                  75                  80 | | 240 |
| gcc gcc gtg gac aca gac tcc ccc cga gag gtc ttt ttc cga gtg gca<br>Ala Ala Val Asp Thr Asp Ser Pro Arg Glu Val Phe Phe Arg Val Ala<br>                85                  90                  95 | | 288 |
| gct gac atg ttt tct gac ggc aac ttc aac tgg ggc cgg gtt gtc gcc<br>Ala Asp Met Phe Ser Asp Gly Asn Phe Asn Trp Gly Arg Val Val Ala<br>            100                 105                 110 | | 336 |
| ctt ttc tac ttt gcc agc aaa ctg gtg ctc aag gcc ctg tgc acc aag<br>Leu Phe Tyr Phe Ala Ser Lys Leu Val Leu Lys Ala Leu Cys Thr Lys<br>        115                 120                 125 | | 384 |
| gtg ccg gaa ctg atc aga acc atc atg ggc tgg aca ttg gac ttc ctc<br>Val Pro Glu Leu Ile Arg Thr Ile Met Gly Trp Thr Leu Asp Phe Leu<br>130                 135                 140 | | 432 |
| cgg gag cgg ctg ttg ggc tgg atc caa gac cag ggt ggt tgg gac ggc<br>Arg Glu Arg Leu Leu Gly Trp Ile Gln Asp Gln Gly Gly Trp Asp Gly<br>145                 150                 155                 160 | | 480 |
| ctc ctc tcc tac ttt ggg acg ccc acg tgg cag acc gtg acc atc ttt<br>Leu Leu Ser Tyr Phe Gly Thr Pro Thr Trp Gln Thr Val Thr Ile Phe<br>                165                 170                 175 | | 528 |
| gtg gcg gga gtg ctc acc gcc tcg ctc acc atc tgg aag aag atg ggc<br>Val Ala Gly Val Leu Thr Ala Ser Leu Thr Ile Trp Lys Lys Met Gly<br>            180                 185                 190 | | 576 |
| tga | | 579 |

<210> SEQ ID NO 6
<211> LENGTH: 192
<212> TYPE: PRT
<213> ORGANISM: Homo sapiens

<400> SEQUENCE: 6

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
            20                  25                  30

-continued

```
Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
            85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
            165                 170                 175

Val Ala Gly Val Leu Thr Ala Ser Leu Thr Ile Trp Lys Lys Met Gly
            180                 185                 190
```